US008078554B2

(12) United States Patent
Fung et al.

(10) Patent No.: US 8,078,554 B2
(45) Date of Patent: Dec. 13, 2011

(54) KNOWLEDGE-BASED INTERPRETABLE PREDICTIVE MODEL FOR SURVIVAL ANALYSIS

(75) Inventors: Glenn Fung, Madison, WI (US); Cary Dehing-Oberije, Brunssum (NL); Andreas Lubbertus Aloysius Johannes Dekker, Maastricht (NL); Philippe Lambin, Genappe-Bousval (BE); Shipeng Yu, Exton, PA (US); Kartik Jayasurya Komati, Sunnyvale, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 148 days.

(21) Appl. No.: 12/506,583

(22) Filed: Jul. 21, 2009

(65) Prior Publication Data

US 2010/0057651 A1 Mar. 4, 2010

Related U.S. Application Data

(60) Provisional application No. 61/093,841, filed on Sep. 3, 2008.

(51) Int. Cl.
*G06N 5/00* (2006.01)

(52) U.S. Cl. ........................................... 706/12; 706/45

(58) Field of Classification Search .................... 706/12, 706/45

See application file for complete search history.

(56) References Cited

U.S. PATENT DOCUMENTS 7,844,560 B2 * 11/2010 Krishnan et al. ................ 706/46
2003/0120458 A1 6/2003 Rao et al.

OTHER PUBLICATIONS

Verduijn, et al., Prognostic Bayesian networks I: Rationale, learning procedure, and clinical use, Journal of Biomedical Informatics, vol. 40, Issue 6, Dec. 2007, pp. 609-618.*

Peek, et al., ProCarSur: A System for Dynamic Prognostic Reasoning in Cardiac Surgery, Artificial Intelligence in Medicine, Lecture Notes in Computer Science, 2007, vol. 4594/2007, pp. 336-340.*

Pfister DG, Johnson DH, Azzoli CG, et al. American Society of Clinical Oncology treatment of unresectable non-small-cell lung cancer guideline: update 2003. J Clin Oncol 2004;22:330-353.

Dehing-Oberije C, De Ruysscher D, van der Weide H, et al. Tumor Volume Combined With Number of Positive Lymph Node Stations Is a More Important Prognostic Factor Than TNM Stage for Survival of Non-Small-Cell Lung Cancer Patients Treated With (Chemo)radiotherapy. Int J Radiat Oncol Biol Phys 2008;70:1039-1044.

Dehing-Oberije C, Yu S, De Ruysscher D, et al. Development and external validation of a prognostic model for 2-year survival of non-small cell lung cancer patients treated with (chemo) radiotherapy. Int J Radiat Oncol Bid Phys (accepted Aug. 2008).

(Continued)

*Primary Examiner* — Wilbert L Starks
(74) *Attorney, Agent, or Firm* — Joshua B. Ryan

(57) ABSTRACT

Knowledge-based interpretable predictive modeling is provided. Expert knowledge is used to seed training of a model by a machine. The expert knowledge may be incorporated as diagram information, which relates known causal relationships between predictive variables. A predictive model is trained. In one embodiment, the model operates even with a missing value for one or more variables by using the relationship between variables. For application, the model outputs a prediction, such as the likelihood of survival for two years of a lung cancer patient. A graphical representation of the model is also output. The graphical representation shows the variables and relationships between variables used to determine the prediction. The graphical representation is interpretable by a physician or other to assist in understanding.

19 Claims, 4 Drawing Sheets

OTHER PUBLICATIONS

Brundage MD, Davies D, Mackillop WJ. Prognostic factors in non-small cell lung cancer: a decade of progress. Chest 2002;122:1037-1057.

D Heckerman, D Geiger, DM Chickering. Learning Bayesian networks: The combination of knowledge and statistical data. Machine Learning, 1995—Springer.

Chickering DM, Heckerman D, Meek C. Large-Sample Learning of Bayesian Networks is NP-Hard. Journal of Machine Learning Research 5 (2004) 1287-1330.

W Lam, F Bacchus. Learning Bayesian Belief networks: An approach based on MDL principle. Computational Intelligence, 1994.

Murphy K. The Bayes Net Toolbox for Matlab, Computing Science and Statistics, vol. 33, No. 2, (2001), pp. 1024-1034.

K. Pelckmans and J. De Brabanter and J. A. K. Suykens and B. De Moor. Handling missing values in support vector machine classifiers. Neural Netwoks Journal. (108) 5-6. 2005.

Alireza Farhangfar and Lukasz Kurgan and Jennifer Dy. Impact of imputation of missing values on classification error for discrete data. Pattern Recognition. (41) 12 . 2008.

Eaton D, Murphy K. Bayesian structure learning using dynamic programming and MCMC. 2007 Proceedings of the 23nd Annual Conference on Uncertainty in Artificial Intelligence (UAI-07).

Pillot G, Siegel BA, Govindan R. Prognostic value of fluorodeoxyglucose positron emission tomography in non-small cell lung cancer: a review. J Thorac Oncol. Feb. 2006;1(2):152-9.

Heckerman D (1998). A tutorial on learning with Bayesian networks. In:Jordan MI, editor. Learning in graphical models. Dordrecht: Kluwer Academic. pp. 301-354.

G. Fung and O. L. Mangasarian. Finite {N}ewton Method for {L}agrangian Support Vector Machine Classification. Special Issue on Support Vector Machines. Neurocomputing, vol. 55, Issues 1-2, Sep. 2003, pp. 39-55.

K. Murphy, "Bayes Net Toolbox for Matlab", Oct. 19, 2007; http://www.sc.ubc.ca/~murphyk/Software/BNT/bnt.html.

Burnside ES. Bayesian networks: computer-assisted diagnosis support in radiology. Acad Radiol. Apr. 2005;12(4):422-30.

Commonly diagnosed cancers worldwide. Cancer Research UK (Apr. 2005).

Hoot N, Aronsky D. Using Bayesian networks to predict survival of liver transplant patients. AMIA Annu Symp Proc. 2005:345-9.

Needham, et al., A primer on learning in Bayesian networks for computational biology. PLOS computational biology, vol. 3, issue 8, pp. 1409-1416, 2007.

SL Lauritzen. The EM algorithm for graphical association models with missing data. Computational Statistics & Data Analysis, 1995.

AJ Hartemink, DK Gifford, TS Jaakkola, RA Young. Bayesian Methods for Elucidating Genetic Regulatory Networks. IEEE Intelligent Systems, 2002.

* cited by examiner

KNOWLEDGE-BASED INTERPRETABLE PREDICTIVE MODEL FOR SURVIVAL ANALYSIS

RELATED APPLICATIONS

The present patent document claims the benefit of the filing date under 35 U.S.C. §119(e) of Provisional U.S. Patent Application Ser. No. 61/093,841, filed Sep. 3, 2008, which is hereby incorporated by reference.

BACKGROUND

The present embodiments relate to predictive modeling for disease. For example, survival from lung cancer is predicted.

Survival or survivability from lung cancer, such as non-small cell lung cancer (NSCLC), is relatively low as compared to some other cancers. One common treatment is surgery to resect tumors. Accordingly, various prognosis techniques are directed to patients to be treated with surgery. However, these techniques may not apply to lung cancer patients treated with radiation and/or chemotherapy. An accurate personalized prediction of survival may stratify cancer patients into different risk groups and help in formulating more personalized treatment strategies.

Patients with stage I-IIIB lung cancer may be treated with curative intent without surgery. Currently, prediction of survival outcome for NSCLC patients treated with chemotherapy and/or radiotherapy is mainly based on clinical factors using TNM staging. However, clinical TNM staging may be inaccurate for survival prediction of non-surgical patients, and alternatives are currently lacking.

To improve risk stratification for non-surgical patients, a number of variables associated with survival have been identified. At present, the generally accepted prognostic factors for survival of inoperable patients are performance status, weight loss, presence of comorbidity, use of chemotherapy in addition to radiotherapy, and tumor size. Retrospective studies suggest that a higher radiation dose leads to improved local control and better survival rates. For other factors, such as sex and age, the literature shows inconsistent results, making it impossible to draw definitive conclusions.

Statistical and data-mining based models for predicting survival may have a promising predictive accuracy given that all the variables needed by the model are known. In reality, predictor variables are usually incomplete due to the data collection process, lack of accurate assessment and knowledge of tumor and patient related factors, or cost limitations related to equipment.

SUMMARY

In various embodiments, systems, methods, instructions, and computer readable media are provided for knowledge-based interpretable predictive modeling of patients. Expert knowledge is used to seed training of a model by a machine. The expert knowledge may be incorporated as diagram information, which relates known causal or correlated relationships between predictive variables. A predictive model is trained. In one embodiment, the model operates even with a missing value for one or more variables by using relationships between variables.

For application, the model outputs a prediction, such as the likelihood of survival for two years of a lung cancer patient. A graphical representation of the model is also output. The graphical representation shows the variables and relationships between variables used to determine the prediction. The graphical representation is interpretable by a physician or other to assist in understanding.

In a first aspect, a system is provided for knowledge-based interpretable predictive modeling of patients. An input is configured to receive patient information representing a characteristic of a first patient. A processor is configured to apply a graphical model as a function of the patient information. The model is configured to output a survival prediction for the first patient. A display is configured to output an image. The image is a graphical representation of the graphical model and the survival prediction.

In a second aspect, a computer readable storage medium has stored therein data representing instructions executable by a programmed processor for knowledge-based interpretable predictive modeling of patients. The instructions include receiving diagram information representing relationships between variables of a disease, seeding a predictive model with the diagram information, training the predictive model, as seeded with the diagram information, with training data, the data comprising values for the variables of the disease, and generating a graphical representation of the predictive model after the training, the graphical representation showing at least one of the relationships.

In a third aspect, a method is provided for knowledge-based interpretable predictive modeling of patients. A graphic model is trained with machine training using training data for a plurality of previous cancer patients. The graphic model is trained to predict survivability of cancer based on relationships between variables from a cancer expert. The training data includes previous patient values for the variables, and the variables include the survivability. A processor applies current patient values of the variables for a current cancer patient to the graphic model. The graphic model is configured to predict even with one of the variables not having a current patient value. A representation of the graphic model is displayed. The representation shows the variables and the relationships remaining after training. The survivability for the current cancer patient predicted by the graphic model is also displayed.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

DESCRIPTION OF PREFERRED EMBODIMENTS

Bayesian, other graphic, or other predictive networks are trained to create personalized predictive models. Unlike some other machine learning based methods such as Support Vector Machines, Bayesian networks naturally reason under uncertainty. The Bayesian network may be used to compute marginal and conditional probability distributions on unobserved nodes and thereby offer a natural way to represent the uncertainties in decision making medical systems. The graphical representation of the network enables a meaningful interpretation of causal or correlated relationships between different attributes and an effective means to reason about new links and graphs. The model may be started based on domain knowledge, such as relationships between variables provided by a physician. This knowledge-based seeding of the model may more effectively create a predictive model.

The model may be used for predicting side effects and/or survivability with or without treatment for any disease. Below, an example embodiment for predicting two-year survival in lung cancer patients is provided. In this example embodiment, a Bayesian network provides a personalized prediction model for two-year survival in patients with inoperable stage I-III non-small cell lung cancer (NSCLC) treated with radiotherapy. In these patients, generally accepted prognostic and predictive factors include performance status (WHO-PS), weight loss, presence of co-morbidity, radiation dose, tumor size and the use of chemotherapy in addition to radiotherapy. Factors such as gender and age have shown inconsistent results in predicting outcome. $^{18}$F-fluorodeoxyglucose positron emission tomography (FDG-PET) and derived factors such as maximal uptake of FDG in the tumor or the number of FDG-PET positive lymph nodes in the mediastinum (PLNS) may be a prognostic variables in NSCLC. However, FDG-PET is not available for all NSCLC patients for a variety of reasons. The predictive models may use the FDG-PET variables when available, but also may be able to predict accurately when these values are missing.

In data tests using this example, Bayesian networks predict the two-year survival in NSCLC patients as accurately as a Support Vector Machines model, but predict survival more accurately in patients in which one or more of the input features are missing.

Figure 1:
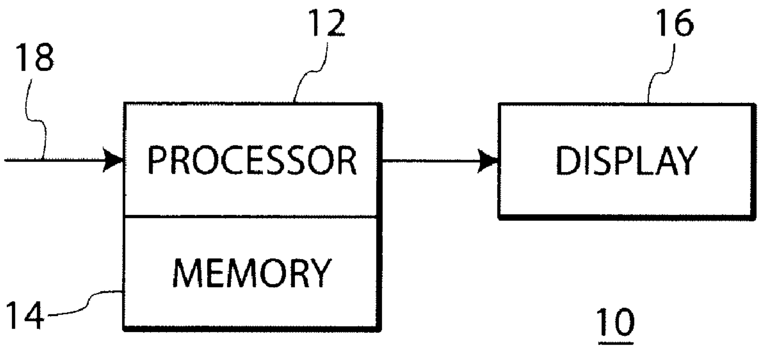
FIG. 1 is a block diagram of one embodiment of a system for knowledge-based interpretable predictive modeling of patients.

FIG. 1 shows a block diagram of an example system 10 for knowledge-based interpretable predictive modeling of patients. The system 10 is shown as a hardware device, but may be implemented in various forms of hardware, software, firmware, special purpose processors, or a combination thereof. Some embodiments are implemented in software as a program tangibly embodied on a program storage device. By implementing with a system or program, semi-automated workflows are provided to assist a user in generating a prediction of treatment outcome and/or recommending radiation dose. Data representing a patient is transformed into an image showing the relationship of variables used to predict side-effects or survivability with treatment or without treatment. The system 10, using a machine, allows prediction for many patients and training of a model based on large data sets as compared to manual determination. For application, the system 10 transforms data representing characteristics of the patient into an output useable by doctors in treatment or therapy planning.

The system 10 is a computer, personal computer, server, PACs workstation, imaging system, medical system, network processor, network, or other now known or later developed processing system. The system 10 includes at least one processor (hereinafter processor) 12, at least one memory (hereinafter memory) 14, a display 16, and at least one input (hereinafter input) 18. The processor 12 is implemented on a computer platform having hardware components. The computer platform may also include an operating system and microinstruction code. The various processes, methods, acts, and functions described herein may be either part of the microinstruction code or part of a program (or combination thereof) executed via the operating system. Additional, different, or fewer components may be provided.

The input 18 is a user input, network interface, external storage, or other input device configured to provide data to the system 10. For example, the input 18 is a mouse, keyboard, track ball, touch screen, joystick, touch pad, buttons, knobs, sliders, combinations thereof, or other now known or later developed user input device. The user input may operate as part of a user interface. For example, one or more buttons are displayed on the display 16. The user input is used to control a pointer for selection and activation of the functions associated with the buttons. Alternatively, hard coded or fixed buttons may be used. As another example, the input 18 is a hard-wired or wireless network interface. A universal asynchronous receiver/transmitter (UART), a parallel digital interface, a software interface, Ethernet, or any combination of known or later developed software and hardware interfaces may be used. The network interface may be linked to various types of networks, including a local area network (LAN), a wide area network (WAN), an intranet, a virtual private network (VPN), and the Internet. The network interface may be linked to the memory 14 or other memory, such as a database of values for patients.

The input 18 is an interface to receive data representing one or more characteristics of one or more patients or to receive data used to derive the characteristics. The data may include clinical information, such as the age, gender, family history, test results, tumor volume, or other information determined to be relevant to the treatment and/or prediction. The data may include volume, blood biomarkers, lung bullae, uptake, or other imaging or test information. Combinations of information may be received, such as both volume and number of positive lymph node stations. Any combination of information may be used. Any derived quantities or raw data may be used, such as a lung volume being provided on the input 18 or an image for deriving lung volume being provided on the input 18.

In the example embodiment, the input 18 receives patient information for one, two or more of tumor load, T-stage, N-stage, number of lymph node stations, and WHO performance. Additional, different, or fewer characteristics may be used for a lung cancer patient. Additional, different, or fewer characteristics may be used for patients associated with other diseases.

The processor 12 has any suitable architecture, such as a general processor, central processing unit, digital signal processor, server, application specific integrated circuit, field programmable gate array, digital circuit, analog circuit, combinations thereof, or any other now known or later developed device for processing data. Likewise, processing strategies may include multiprocessing, multitasking, parallel processing, and the like. A program may be uploaded to, and executed by, the processor 12. The processor 12 implements the program alone or includes multiple processors in a network or system for parallel or sequential processing. The processor 12 is configured by the program or by design to perform the functions, acts, or processes described herein.

The processor 12 creates a model, applies the model, or both creates and applies the model. The model is of survivability and/or side-effects in response to no therapy, chemotherapy and/or radiation therapy. The model may or may not account for the radiation plan, such as the MLD or other dose parameter.

In one embodiment, the model is a machine-learned model. For example, a model predicting survivability is machine trained. As another example, a model predicting injury is machine trained. Any machine-learning algorithm or approach to classification may be used. In one embodiment, the model is a graphical model. For example, a Bayesian network, Hidden Markov, linear dynamic system, Kalman filters, random fields, combination thereof, or other now known or later developed machine learning graphic model is provided. The machine learning provides an output. The output is derived from analysis of a database of training data with known results, such as a database of data with binary or a larger range of possible labeled outcomes. The machine-learning algorithm determines the relationship of different variables or nodes to each other. One of the nodes is the result. The learning may select only a sub-set of variables (i.e., input features) or may use all available input features.

A programmer may influence or control which input features to use or other performance of the training. For example, the programmer inputs relationship information and/or selects variables to be used, at least initially. The relationships are links between the variables. For example, the T- and N-stage variables from TNM staging indicate a higher or lower count of positive lymph node stations. The T- and N-stage variables are causally linked to the number of positive lymph node stations. An expert may provide this graphical information. The machine learning determines the probability associated with the relationship and probabilities associated with each variable. The variables and links for a graph of variables connect with the outcome, providing a graphical model for classifying. Domain knowledge from literature or experts in the field, such as lung cancer specialists, is used to seed the learning. Machine training allows for weighting, verification and/or creation of interrelationships not easily performed manually.

The domain knowledge is manually programmed as a seed. The machine learning determines the strength of the relationships and may or may not add or remove relationships and/or variables. The model may be validated using machine training.

The model represents a probability of survivability, side-effects, or both. This probability is a likelihood for the disease of interest, such as non-small cell lung cancer. The likelihood is modeled from any lung cancer patient information. Any limitation may be used, such as a one-year, two year, three year, or other term of survival. For example, the model predicts the likelihood of grade three as opposed to all other (no, grade one and grade two) grades of pneumonitis. Other probabilities may be used. Any period may be used for measuring whether injury has occurred, such as 90 days after completion of treatment. Alternatively, the probability is based on measurements during treatment, such as for reoccurrence or after exposure to a partial dose.

Different probabilities may be learned based on any input or output levels. The possible values may be grouped, such that a different model is provided for different input ranges and/or output possibilities. For example, probability of injury is determined for each of four possible grades. More or fewer levels of increment may be provided. Each probability indicates the likelihood of injury at a certain level (e.g., probability x for grade 3, y for grade 2, w for grade 1, and u for no injury where each probability is based on a different model).

The probabilities associated with the variables and relationships are learned or derived from data of other patients, training data. The training data may be from a hospital or study. Alternatively, a network of hospitals or different databases is provided. Information from the different databases may be secured, kept private, and/or made anonymous (e.g., removal of patient identifiers) for training.

The database of other patients includes clinical, imaging, and/or other data from before therapy and at the desired time after or during therapy. The dose applied to the tumor and/or regions of the tumor for treatment may be included. Other features may be provided, such as age, gender, WHO performance, lung function (e.g., expiration volume), tumor type, and tumor size. Different feature vectors may be provided for different types of tumors, different models, and/or different probabilities (e.g., side-effects versus survival).

For the training data, injury is measured subjectively, such as by a medical practitioner, or objectively, such as by the results of a test. Tissue or an image may be examined for pneumonitis or other injury. Alternatively, the processor 12 determines injury. For example, CT image information is analyzed to identify injured segments or regions. For survival training data, user entry of the binary indication of survival is used. Alternatively, the survival information is mined from other sources or determined by other evidence (e.g., a visit more than two years after treatment) by the processor 12.

Input feature information may be normalized. For example, uptake values are normalized based on uptake for healthy tissue. The model is trained based on normalized values.

The training, learning, or development of the model occurs at a developers facility or by a developer at any facility. In alternative embodiments, the model is updated and/or trained at a customer location. For example, additional training data is made available at a hospital, such as due to ongoing treatment of patients at the hospital. The model may be relearned, modified, or created again based on the additional data available to a customer. The model adapts to information available at a site of use. The processor 12 applies the model or models. The graphical model is applied using patient information. Data for a given patient or group of patients is input for application. The input is by manual entry, transfer, mining, or other input. For example, data from fields in a computerized patient record is loaded for application to a graphical model for non-small cell lung cancer.

Values for the available variables of the graphical model are input into the model or models. The information may be input according to requirements, such as inputting values in specific units. Alternatively, raw data is input, and the model includes preprocessing to derive the values used to train the model. For example, a ratio of lung bullae to a lung volume is determined from input CT image data.

Different inputs may be used for different models. For example, two-year survivability is predicted using a feature vector of tumor load, T-stage, N-stage, number of positive lymph node stations, and WHO score. The graphical model links the variables. Links extend from a tumor load node to a T-stage node, a N-stage, and a survival node, from the T-stage node to a number of positive lymph node stations node, from the N-stage node to the number of positive lymph node stations node, from a who score node to the survival node, and from the number of positive lymph node stations node to the survival node. Survivability for other terms or injury prediction may use different features and/or links.

The data is input to the graphical model. The graphical model may be a table, matrix, or other data implemented by the processor 12. In one embodiment, the graphical model is a machine-learned Bayesian network which was learned from a seed. The seed for training the graphical model is from an expert in a medical domain. The seed for training represents relationships between variables.

Missing data may be substituted with an average, median, default value, or an expectation based on other inputs, or more sophisticated models may be used to impute missing data. For example, the median or mean learned from the training data for a given variable is used. As another example, the probabilities associated with relationships to connected variables and the values of the connected variables are used to calculate the missing value. Alternatively, missing data may be left blank where the model may still provide sufficient accuracy.

In response to the input, the model outputs a probability. The output is a survivability prediction. For example, the likelihood of a patient surviving for two years after treatment is output. Alternatively or additionally, the output is a side-effect prediction. For example, the likelihood of a patient suffering from pneumonitis is output. The processor 12 outputs the probability or probabilities for creating or using the models. The output may be a binary decision rather than a probability, such as a prediction of survival or not. The processor 12 outputs the data to the display 16, to the memory 14, over or to a network, to a printer, or in other media. Other outputs may be provided, such as confidence intervals, error information, standard deviation, or other data associated with the probability.

The processor 12 outputs a representation of the graphical model. A diagram showing the variables and links between variables is displayed on the display 16. Alternatively, the variables and links are represented in a table or list. The representation provides understandable relationships so that a user may perceive the causes or reasons for the prediction.

The output and/or inputs may be displayed to a user on the display 16. The display 16 is a CRT, LCD, plasma, projector, monitor, printer, or other output device for showing data. The display 16 is configured to display an image. The image may be of a medical image, a user interface, charts, graphs, values, or other information, such as the side-effects prediction, survivability prediction, or both. For example, the display 16 outputs an image generated with information output from the model for the lung cancer patient. The image shows the predicted likelihood with or without other information. The likelihood is based on data specific to or representing a given patient. More than one likelihood may be output, such as a graph representing the probability of survival as a function of time or the probability of side-effect as a function of dose. The display is text, graphical, or other display.

Supporting information, such as values, different model outputs, options, or other supporting information, may be displayed. In one embodiment, the output image includes a graphical representation of the graphical model with or without the survival prediction. The graphical representation shows the nodes and the links. The probabilities associated with the nodes and/or links may also be displayed, such as displaying the base probability and the variance. The values of the variables for each node may be displayed. Missing values may be indicated as blank or with a highlighted or labeled substitute value. For example, the nodes are associated and labeled with respective characteristics of the patient, a value for each characteristic is included with the respective node, and links connect between some nodes and not between other nodes. The links represent the causal and/or correlated relationships of the graphical model.

The processor 12 operates pursuant to instructions. The instructions, graphical model, matrix, image data, clinical data, patient characteristics, values, and/or patient record for knowledge-based interpretable predictive modeling of patients are stored in a computer readable memory, such as external storage, memory 14 (e.g., cache, system memory, ROM and/or RAM). The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Because some of the constituent system components and method acts depicted in the accompanying figures may be implemented in software, the actual connections between the system components (or the process steps) may differ depending upon the manner of programming.

The same or different computer readable media may be used for the instructions, the individual patient data, the model, and the database of previously treated patients (e.g., training data). The patient records are stored in the external storage, but may be in other memories. The external storage or the memory 14 may be implemented using a database management system (DBMS) managed by the processor 12 and residing on a memory, such as a hard disk, RAM, or removable media. The external storage may be implemented on one or more additional computer systems. For example, the external storage may include a data warehouse system residing on a separate computer system, a PACS system, or any other now known or later developed hospital, medical institution, medical office, testing facility, pharmacy or other medical patient record storage system. The external storage, an internal storage (memory 14), other computer readable media, or combinations thereof store data for at least one patient record for a patient. The patient record data may be distributed among multiple storage devices.

In other embodiments, the system 10 connects with a structural imaging system, a functional imaging system, a blood testing system, and/or a therapy applicator (e.g., linear accelerator). For example, the system 10 connects with a CT-PET system and a linear accelerator for radiation therapy. The imaging system scans the patient and provides data representing the scanned region of the patient for transformation by analysis. As another example, the system 10 connects with a blood testing system or database from a blood testing facility. The data is provided for transformation by modeling. The system 10 assists the user in planning therapy. The output information may be used to select between receiving radiation therapy or not and/or to select appropriate dose. The system 10 is part of one of these components and/or communicates with the components to acquire image data and control treatment. For example, the processor 12 communicates a fraction of a treatment plan to the linear accelerator, controlling application of radiation to the patient.

Figure 2:
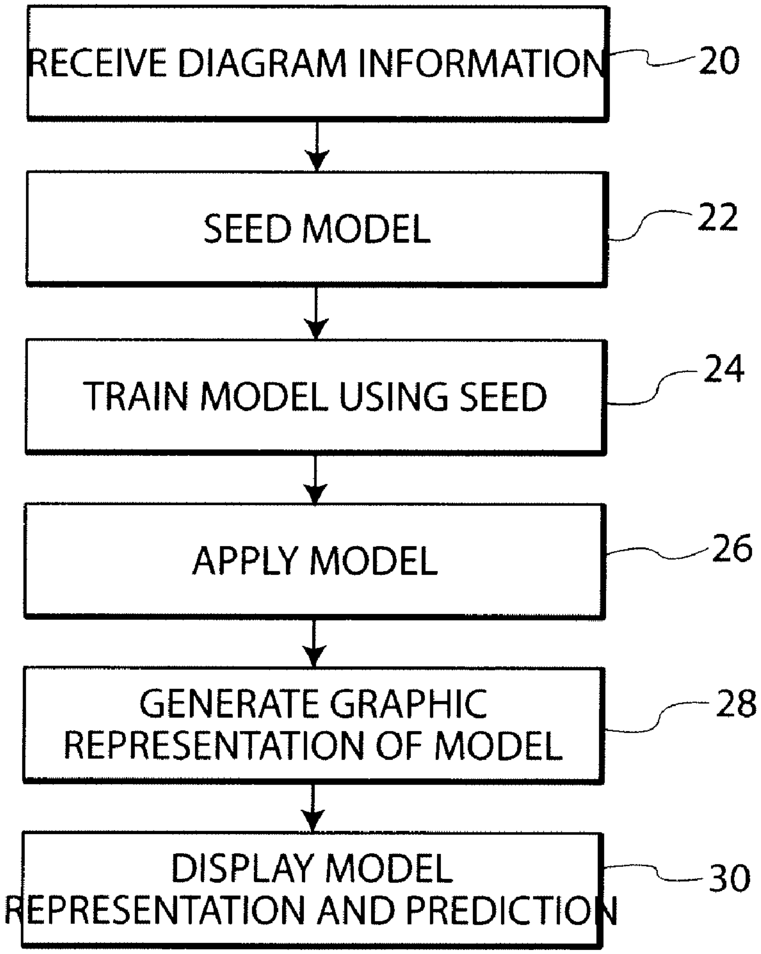
FIG. 2 is a flow chart diagram of one embodiment of a method for knowledge-based interpretable predictive modeling of patients.

FIG. 2 shows a method for knowledge-based interpretable predictive modeling of patients. A model is created and/or applied using patient information. Any patient information may be used, such as clinical characteristics, treatment, imaging, tumor and/or other information. Patient clinical characteristics may include age, gender, co-morbidities, performance score (WHO, Karnofsky) or others. Tumor characteristics may include staging (e.g., tumor-node-metastasis (TNM) staging according to the American Joint Committee on Cancer, AJCC), size, shape, number, location, histology, or others. Treatment information may include regime, dose, time, type, medicine, or others. Imaging information may include gross tumor volume (GTV), standard uptake value (SUV), or others.

The method is implemented with the system of FIG. 1, or a different system. The same or different systems may perform creating and applying the models. For example, one computer is used for development, and a different computer is used for applying the developed models. The models may be developed, and then sold or otherwise distributed for application by others. As another example, users of the developed models are charged. Users request predictions from the developer, so the model is applied by the same computer used for development or by different computer controlled by the developer.

The acts are performed in the order shown or a different order. Additional, different, or fewer acts may be provided. For example, acts 20, 22, and 24 are not provided. Acts 20, 22, and 24 generally correspond to training a model using a seed. In alternative embodiments, the model is trained without input domain knowledge. In another example, acts 26, 28, and/or 30 are not provided. Acts 26, 28, and 30 generally correspond to application of the model. The model may be applied without generating a graphic representation.

In act 20, diagram information is received. The information is received by a computer, such as through manual entry or data transfer.

The diagram information represents relationships between variables of a disease. For example, the disease is lung cancer. The diagram information includes variables and/or links. Variables are received, such as receiving tumor load, T-stage, N-stage, number of positive lymph node stations, WHO performance, and survival for seeding a model to predict survival. Links between the variables are received. For example, links from a tumor load node to a T-stage node, a N-stage, and a survival node, from the T-stage node to a number of lymph node stations node, from the N-stage node to the number of lymph node stations node, from a who score node to the survival node, and from the number of lymph node stations node to the survival node are received.

The diagram information is received in any form. For example, the diagram information is input in a graphical programming interface. In another example, the diagram information is input as a table or list.

The diagram information is from an expert in the relevant medical domain. For example, one or more physicians with experience treating lung cancer are requested to indicate predictive characteristics and whether the different characteristics have a causal or correlated relationship. The experts may be requested to diagram their knowledge. As another example, the diagram information is derived from literature. The diagram information obtained from the expert is formatted as appropriate for use by the computer. In alternative embodiments, the diagram information is not used or is derived from machine learning.

In act 22, the model is seeded. A predictive model is initialized with the diagram information. For example, a Bayesian network is configured to correspond, at least initially, to the diagram information from the domain knowledge. Data-driven structure learning algorithms exist that infer the graphical network representing the underlying data distributions. Because the space of structures is very huge, a sufficient amount of training samples are necessary to model complex relationships and avoid over fitting. Determining patient survival status usually spans a considerable amount of time. However, major diseases in the field of medicine are well studied and documented, which combined with doctor's knowledge and experience, provides available prior knowledge that can be incorporated to compensate for the limitation in the amount of available data. Seeding may allow for sufficient modeling with less training data.

In act 24, the predictive model is trained. The model is trained, as seeded with the diagram information, with training data. Machine training is used due to the large amount of data. Manual training may be prohibitive. The model is trained to predict a value for one of the variables, such as training a graphic model to predict survivability of cancer based on relationships between variables from a cancer expert. The model may be created using any type of feature vector. Different feature vectors may be attempted to select a more deterministic group of features.

In one embodiment, a Bayesian network-based predictive model is trained for prediction of 2 year survival in non-small cell lung cancer. Bayesian networks (BN) are formally directed acyclic graphs in which each node in the graph represents a random variable and the links between the nodes specify the direction of the influence. A node in the graphical model encodes either discrete or continuous probability distributions. For example, the parametric form is restricted to only having continuous distributions represented as Gaussian random variables. Continuous modeling limits the number of learnable model parameters to scale linearly in number of nodes. The mean of the continuous distribution is taken as a linear combination of states of node parents, and the second node parameter is the variance of the conditional distribution. Bayesian network learning and inference may be implemented with any now known or later developed program, such as Matlab using BNT's Kevin Murphy toolbox.

Learning the structure of a Bayesian network is an NP hard problem. The search space of graphs is multimodal, grows rapidly with the number of nodes, and may be prone to stick in many local optima. Any search algorithm may be used, such as Markov Chain Monte Carlo (MCMC) local search method included in the BNT toolbox. The MCMC may converge to a locally optimal structure faster than other methods, resulting in more accurate structure learning and higher predictive likelihoods on test data. Other methods for inferring the graphic model may be used, such as variable elimination, dynamic programming, Monte Carlo sampling, variational methods, or belief propagation.

The machine training learns parameters. Any parameter learning may be used. For example, the expectation maximization algorithm (EM) included in the BNT toolbox is used. EM is a search algorithm well suited to the presence of missing values in the dataset. The method alternates between E and M steps to compute the maximum likelihood estimates of the parameters. During the E step, the missing values are assumed by the expectations of the random variables conditional on observed data and parameters. The M step involves computation of expectation of conditional log likelihood of complete data with respect to posteriors of hidden variables and maximizing the log likelihood to find the new estimates of parameters. This process is repeated until convergence. Any convergence criteria may be used, such as an amount of increase of log likelihood value in consecutive iterations. Log-likelihood of the data increases after each iteration. The algorithm starts with random initializations of model parameters to converge onto the optimal point estimates.

In one embodiment, the predicted variable is survivability, such as 2-year survival of non-small cell lung cancer. The network structure is learned from a 5 variable-draft structure of the model, based on literature knowledge and prior medical experience using the following variables: number of positive lymph node stations on a PET or other scan (PLNS), WHO performance scale (WHO-PS), T-stage, N-stage and tumorload (from PET). The seed includes links between the nodes. The BN algorithm is applied to estimate the weights of the variables. The results are represented as a directed acyclic graph in FIG. 3. Higher values of WHO-PS, tumorload and PLNS have a negative impact on the patient's survival prognosis. The variables and links of FIG. 3 correspond to the seed, and the numerical values are the link probabilities learned from the training data set. The machine learning may test, add, and remove variables and/or lines. In this example, the performance of the model does not improve by adding (one or a combination of) the following other clinical available variables: radiotherapy treatment dose, forced expiratory volume (FEV1), weight loss, age, or gender to the network. Accordingly, the learned graphical model uses the variables and links of the seed without adding complicating variables with little added benefit. In alternative embodiments, one or more of these or other variables are included.

Figure 3:
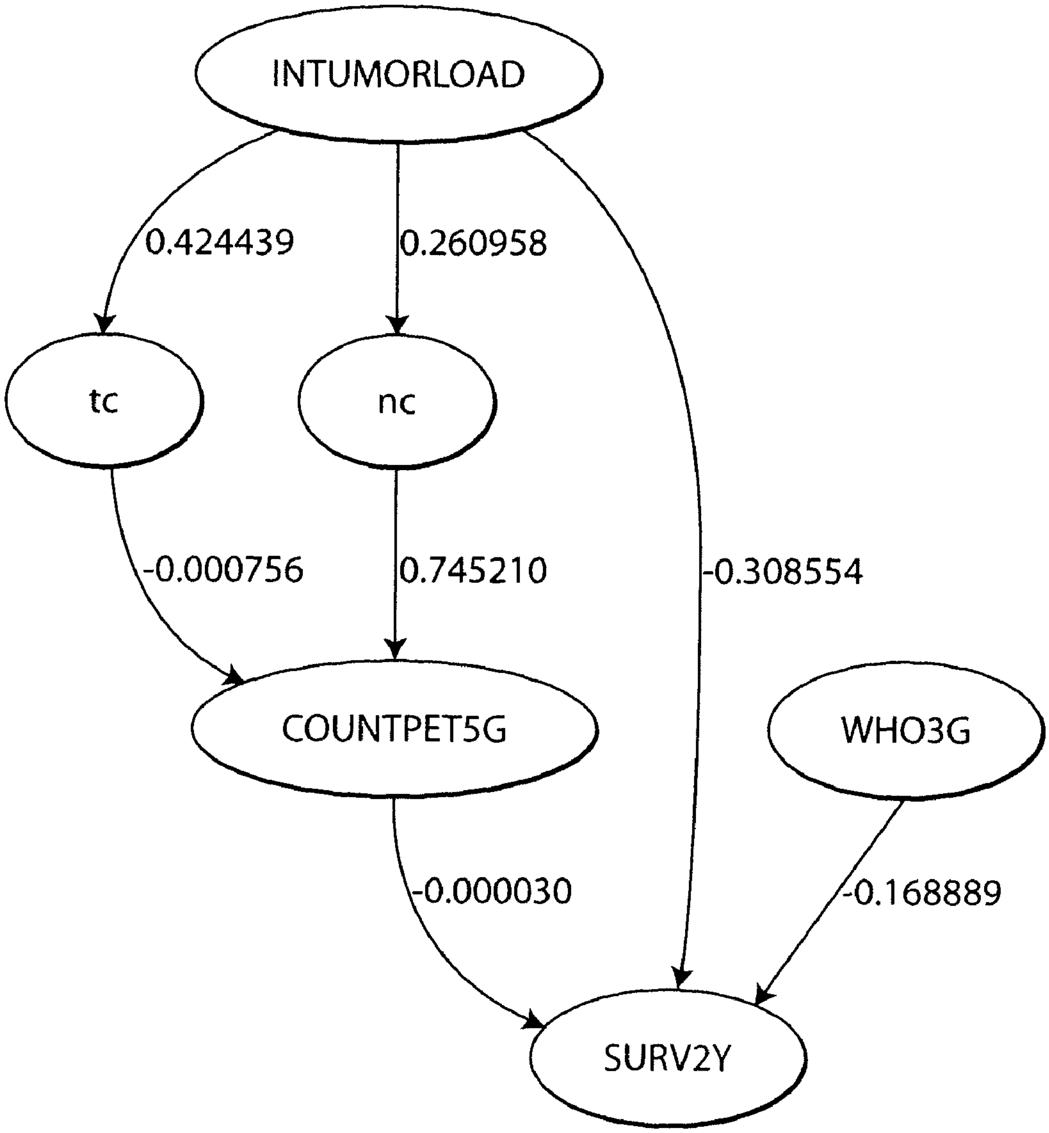
FIG. 3 is an example graphical representation of a predictive model.

FIG. 3 represents the trained directed acyclic graph with weights corresponding to each relationship and represents a complete statistical model. The means and variances for each feature along with the link weights are learned iteratively via an EM algorithm to converge onto their point estimates maximizing the likelihood of the observed data. A positive link weight between two nodes, nodes 1 and 2, means that an increase in the value of node 1 causes the node 2 value to increase. A negative link weight indicates a decrease in value of node 2 when node 1 increases. The absolute value of the weights is a measure of strength of influence by any parent on its child. For example, tumorload (−0.308), WHO-PS (−0.168) and PLNS (−0.00003) are negatively correlated with survival as increasing values of these variables are expected to lower the survival time of the patient.

The difficulty or processing time may vary with the amount of training time, the number of nodes, and the number of links. For example, the graphic model of FIG. 3 seeded with the nodes and variables in FIG. 3 may have an average training time to learn the maximum likelihood estimates of parameters of about 67 seconds on a 1.66 GHz Intel processor with 1 GB of RAM.

The machine training uses training data for a plurality of previous cancer patients. Any number of patients may be included in the training data. The training data includes values for the variables of the disease, such as tumor load and others. Data for a particular patient included in the training data may or may not include the same variables as others. For example, one or more patients may not have had a count of the number of positive lymph node stations. The training data used for training may exclude data for patients with incomplete information, or may include the data.

In the example above, the training cohort includes inoperable I-IIIB NSCLC patients treated with curative intent in MAASTRO Clinic between May 2002 and January 2007 with survival scored in December 2007. In all patients, PET is used as a staging tool (i.e., to determine the T and N stage values), and patients with a follow-up period shorter than 2 years are not taken into account. A total of 322 patients are available for training. For each patient, the gross tumor volume of the primary tumor (GTVprimary) and involved nodes (GTVnodal) are delineated by a radiation oncologist on a planning CT with the PET information available. Tumorload is defined as the sum of GTVprimary and GTVnodal. The number of positive lymph node stations on the PET scan (PLNS) is assessed by a nuclear medicine specialist. Clinical T-stage and N-stage are assessed according to the standard UICC TNM staging system. In patients receiving sequential chemoradiation, the GTV delineation is performed on the post-chemotherapy images for the primary tumor, whereas the initial involved lymph node areas are always included in the GTV. Stage and PLNS is assessed using pre-chemotherapy imaging information.

The training data is labeled as appropriate for the desired outcome, such as indicating survival and/or a particular level of side-effects. The machine-learning algorithm or algorithms are selected. Any now known or later developed algorithm and process for training may be used.

The trained classifier may be validated using the training data. Any validation may be used. For limited training data sets, random selection of training and testing data may be used in many iterations to create a more reliable model. A five-fold or other cross validation is performed on patient-data. A leave-one-out approach may be used. As another example with a large training data set, a group of patients may be used for validation and not for training.

In another embodiment, the trained classifier is validated using a separate set of training data. For example, the external validation cohorts include NSCLC patients, stage I-IIIB, treated with (chemo) radiotherapy from three centers. The Leuven validation cohort includes 35 patients treated in 2005 at the radiotherapy department of the University Hospital Leuven in Belgium. The Ghent validation cohort includes 47 patients treated between May 2003 and December 2005 at the University Hospital Ghent in Belgium. The Toronto cohort includes 33 patients treated between December 2004 and December 2005 at the Princess Margaret Hospital in Toronto, Canada. In all patients, survival at two years is available. The Ghent and Leuven cohort are staged using PET information and have the variable PLNS available, while a PET is not available in the Toronto cohort. For performance assessment, a subset is created in which patients with one or more missing variables (other than PLNS) are removed. Removal results in 37, 28 and 24 patients for the Ghent, Leuven and Toronto cohort, respectively. As the Leuven and Ghent cohort are consistent in the available features, both the individual and a combined Leuven+Ghent sets are used as validation sets in the analysis.

Once created, the model or models are incorporated onto a computer, such as into hardware, software, or both. The incorporation allows operating, with a processor, combined models, or a single model. Values for the feature vectors of the models are obtained. The medical record, functional imaging data, and/or other source provide values for a specific or individual patient. The model is applied to the individual patient information.

In act 26, the trained predictive model is applied. After training, the model may be applied to patient information for one or more patients. Information for the patients is received. The information is obtained from a scanner, such as positive lymph node stations and/or tumor load. Alternatively, the information is obtained from memory, such as previously acquired data transferred from a PACS database or a computerized patient record.

The feature information is received in response to a request. For example, a processor requests acquisition of the data by a scanner or from a database. In response, the requested information is transferred to and received by the processor. Alternatively, the information is pushed to the processor. The receipt may occur in response to user input or without direct user input. The data input corresponds to the predictors or variables used by the models. For example, clinical values are received.

The data is input manually. Alternatively, the data is mined from a database. A processor mines the values from a medical record of the individual patient. For example, the mining discussed in U.S. Published Application No. 2003/0120458, the disclosure of which is incorporated herein by reference, is used. Structured clinical data is mined from unstructured and structured information. If values are available from unstructured data, the values may be mined by searching or probabilistic inference. Other mining may be used, such as acquiring data from a structured computerized patient record (CPR). The mined and/or manually input values are applied to the models to obtain a prediction.

The model outputs an expected outcome for the particular patient, such as a probability of survival over two years given or not given chemo-radiation therapy. The values available for the current patient (e.g., a cancer patient) are input to a computer, such as by manual data input and/or data transfer. The processor calculates the result from the values and the learned probabilities or matrix of the model, such as a graphic model. In alternative embodiments, the user calculates the result using the graphic model.

The model is used to answer probabilistic queries on variables in the network. For example, survival is predicted. Probabilistic inference, the process of computing the posterior of a given node or a subset of nodes in light of evidence observed on the remaining variables, provides the probability of survival given the observed patient values included in the network structure. For exact inference, the junction tree algorithm is used, but other algorithms may be used.

The model may be for any type or combination of types of treatment. Treatment may be a lack of further action, chemotherapy, type of drug, amount of drug, radiation, type of radiation, radiation timing, or other treatment, or treatment combination.

The graphic model predicts even with one of the variables not having a value for the current patient. The model may use a value associated with a variable in a position of stronger evidence. For example in the graphical model of FIG. 3, the T- and/or N-stage values are not available. The links in the model show that the countpet value is stronger evidence as the count feeds directly to the survival node, and the T- and N-stage values are used to predict the countpet value. Since the countpet value is available, the T- and N-stage values may not be used.

In another example, a substitute value is provided for the one of the variables. The substitute value may be selected from a distribution learned from the training data. For example, the WHO value is not available. The average WHO from the training data is used. Alternatively, the missing value is inferred from the probabilities for linked variables and their values. The parameters of the model structure may be learned iteratively in the presence of missing feature values. Missing values may be handled in a robust way without the need for explicit imputation. When missing values are inferred, the performance is superior compared to the performance obtained with traditional imputation methods in other modeling techniques. The model is inherently robust to changes in data and may be used when a variable is completely missing. Bayesian network or other graphical models are more appropriate to use in daily clinical practice as full data collection on a patient is not always possible or practical. Other substitute values may be used, such as a default value assuming a worst or best case.

In act 28, a graphical representation of the predictive model is generated after the training. The graphical representation indicates at least one of the relationships between variables. Graphical models offer a graphical viewpoint to the underlying processes involved in predicting the outcome. The model structure and weights representing influences may be clinically meaningful and easily interpretable by physicians and radiologists. The graphical framework may incorporate prior knowledge and be quickly used to test a new hypothesis and/or a new model. For example, a new link and/or variable are added. The graphical model may be trained using the new seed information to determine performance through validation. The prognosis framework may be easily extended to other domains using knowledge experts who are comfortable building an intuitive initial network.

In act 30, a prediction output by the predictive model is displayed. By applying the graphical model, the output predication is provided to the user. For example, the survivability for the current cancer patient predicted by the graphic model is displayed. A binary indication may be displayed, such as yes or no to "likely to survive two years." The probability information may be displayed. The likelihood from the prediction is output. The display is an image of a report indicating the likelihood with or without any corresponding parameters, such as the term (e.g., two year survival). A table, graph, or other output may be provided. Different likelihoods given different values of one or more variables (e.g., features or models) may be output. The image represents a possible condition of the patient and associated probability of that condition.

The output is to a display, such as an electronic display or a printer. The output may be stored in memory or transferred to another computer. In one embodiment, the likelihood information is output for use with a radiotherapy Treatment Planning System (TPS), in order to optimize the radiation treatment. For example, a dose level with the greatest survivability for a given patient is identified. The dose information is included in a treatment plan. The doses are fractionalized, and the treatment information is transferred to a linear accelerator. In response, the linear accelerator applies radiation to the tumor regions.

The predicted outcome may be displayed alone or with a graphical representation. The graphical representation may be displayed alone or with the predicted outcome.

A representation of the graphic model may be displayed. The representation shows the variables and the relationships remaining after training. For example, the graphical model of FIG. 3 is displayed as the nodes and links, the nodes representing variables and the links representing relationships between the variables. Links are shown between some nodes and not between other nodes. The links represent variables that correlate with other variables for determining the outcome. For example, the T- and N-stage variables may be predicted from the tumor load, but not from the WHO score.

Other information than the links and variables may be displayed. The values input for the current patient may be displayed. The link probabilities may be displayed as shown in FIG. 3. Statistical information associated with the variables and/or links may be displayed. In other embodiments, the graphical model is provided without other information.

By displaying the graphical representation of the predictive model, users may better appreciate the reasons for the prediction. The seed and the resulting trained graphical model may be easily comprehended by a physician and/or patient to better understand the results. Rather than being a "magical" black box prediction, the values leading to the prediction and their relationship with each other may be viewed. By displaying the probability values for the links, the weight of contribution is also reflected. The influence of missing values may also be viewed and understood.

FIGS. 4-7 show performance for one embodiment of non-small scale lung cancer using a Bayesian Network trained model seeded with the variables and links shown in FIG. 3. The model is tested and validated with the help of three independent sets obtained from various medical institutions and countries. The performance of the Bayesian network is determined. The MAASTRO cohort is randomly split into 70% patients in training and remaining 30% to assess the training performance of the model. This procedure is repeated 50 times and shows a mean AUC of 0.72 for the BN model. Table 1 shows the external validation using the data of Toronto, Ghent, Leuven and Ghent+Leuven which yielded AUC values of 0.70, 0.77, 0.72 and 0.75. The Area-Under-the-Curve (AUC) of the Bayesian Network model for the prediction of 2 year-survival in NSCLC patients in three external validation sets, using all patients, is provided. The AUC when using all features and the AUC when the Positive Lymph Node Stations (PLNS) is omitted from the validation dataset are provided.

TABLE 1

| | Toronto | Ghent | Leuven | Ghent + Leuven |
|---|---|---|---|---|
| All features | 0.70 | 0.77 | 0.72 | 0.75 |
| Without PLNS | 0.70 | 0.75 | 0.75 | 0.75 |

In a Bayesian network, the distribution of any node is only dependent on the node's parents assuming that parent nodes are fully observed. When PLNS is not observed (i.e., no value provided for the variable), the factors that influence the survival extend beyond PLNS to the parent nodes: T and N-stage factors. Since the strongest evidence is not available, the related variables are used to infer PLNS. To test the model performance in the absence of PLNS, the feature is treated as a hidden variable in the Ghent and Leuven datasets (in the Toronto set PLNS is not available for every patient), yielding AUC values of 0.70, 0.75, 0.75 and 0.75 for the four sets, as shown in Table 1. When the validation set only contains patients in which the data collection is complete, a slightly better AUC may be found as shown in Table 2.

TABLE 2

| | Toronto | Ghent | Leuven | Ghent + Leuven |
|---|---|---|---|---|
| All features | 0.71 | 0.75 | 0.82 | 0.77 |
| Without PLNS | 0.71 | 0.75 | 0.80 | 0.77 |

Table 2 shows the Area-Under-the-Curve (AUC) of the Bayesian Network model for the prediction of 2 year-survival in NSCLC patients in three external validation sets, using only patients in which the data collection was complete. Shown is the AUC when using all features and the AUC when the Positive Lymph Node Stations (PLNS) is omitted from the validation dataset.

Figure 4:
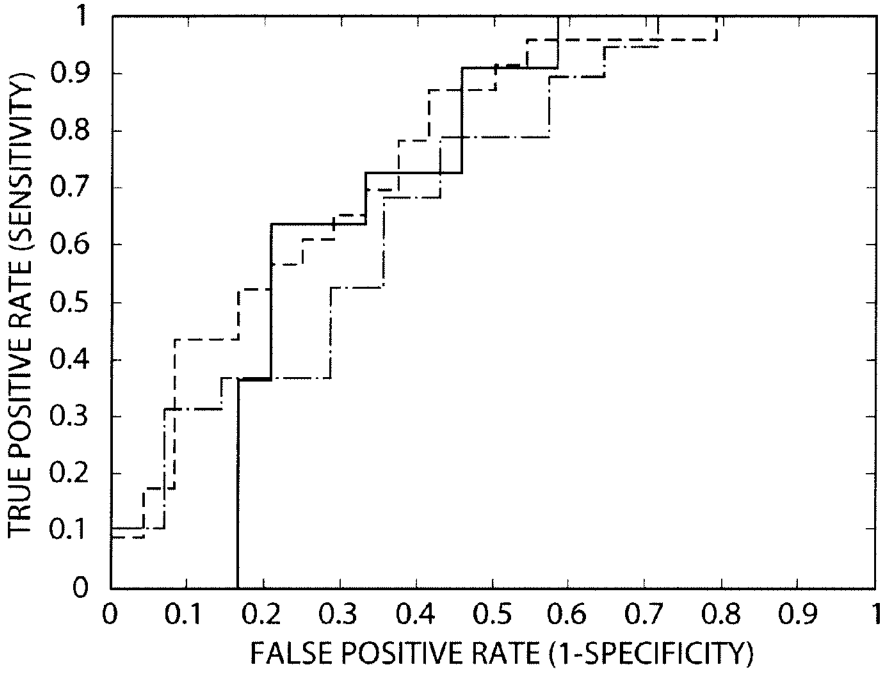
FIG. 4 shows example receiver operating characteristics (ROC) for predicting 2 year survival in non-small cell lung cancer patients using all patient data regardless of whether values are available for all variables.
Figure 5:
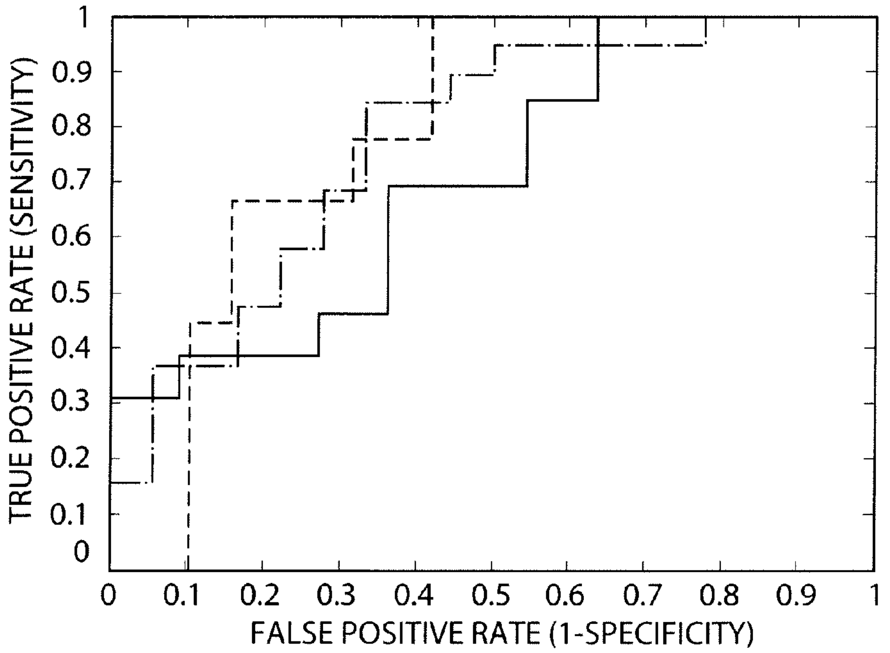
FIG. 5 shows example receiver operating characteristics (ROC) for predicting 2 year survival in non-small cell lung cancer patients using patient data for patients with values available for all variables.
Figure 6:
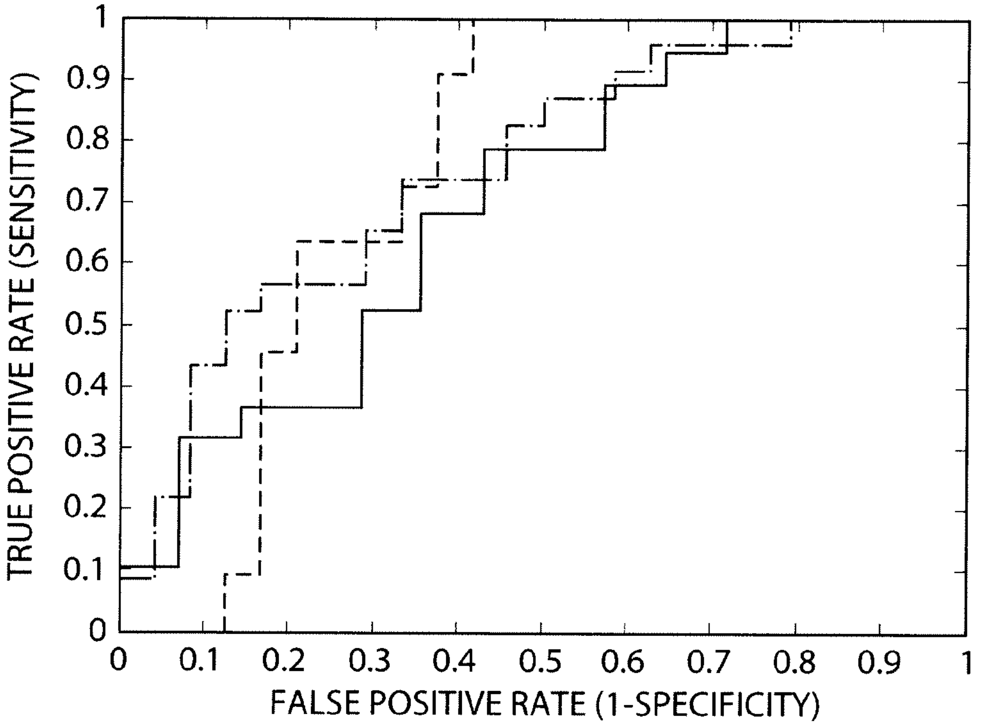
FIG. 6 shows example receiver operating characteristics (ROC) for predicting 2 year survival in non-small cell lung cancer patients with values for all variables except the number of positive lymph node stations.
Figure 7:
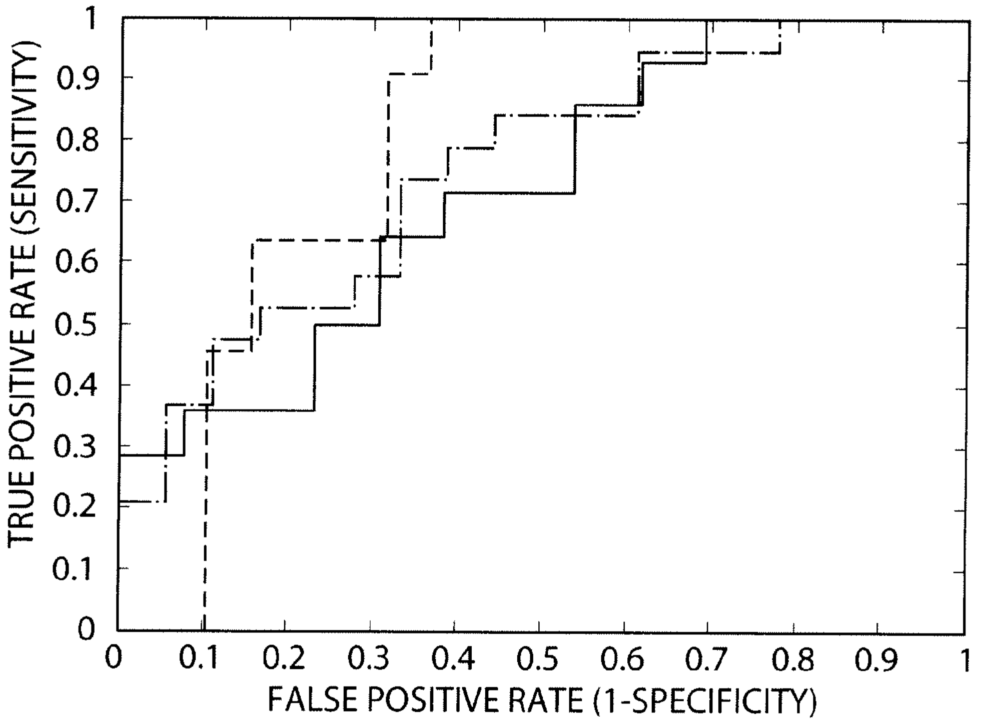
FIG. 7 shows example receiver operating characteristics (ROC) for predicting 2 year survival in non-small cell lung cancer patients using only patient data for patients with values available for all variables, but not using the values for the number of positive lymph node stations.

FIG. 4 shows example receiver operating characteristics (ROC) for predicting 2 year survival in non-small cell lung cancer patients using all patient data regardless of whether values are available for all variables. FIG. 5 shows example receiver operating characteristics (ROC) for predicting 2 year survival in non-small cell lung cancer patients using patient data for patients with values available for all variables FIG. 6 shows example receiver operating characteristics (ROC) for predicting 2 year survival in non-small cell lung cancer patients with values for all variables except the number of positive lymph node stations. FIG. 7 shows example receiver operating characteristics (ROC) for predicting 2 year survival in non-small cell lung cancer patients using only patient data for patients with values available for all variables, but not using the values for the number of positive lymph node stations.

A comparison of Table 1 and 2 and also the associated receiver-operating curves in FIGS. 4-7 show that the Bayesian network model is consistent in performance even in the presence of missing values. A maximum decrease in AUC observed is within 2% and similar ROC curves result.

The model performance is statistically comparable to other well-known modeling techniques, such as support vector machines. For example, a support vector machine (SVM) model is trained to predict whether or not a patient survived after 2-years. The SVM is trained with the same variables as the Bayesian network model so that a fair comparison is possible. In order to train the SVM-based model, publicly available code for a finite Newton method for Lagrangian SVM classification [http://www.cs.wisc.edu/dmi/svm/nsvm/] is used. The model is a binary classifier and does not provide probability of survival, instead predicting whether or not a patient will survive after two years. In the presence of missing values, the standard simple imputation method (mean among the values in the training set) is used in the SVM.

On the MAASTRO cohort, the SVM model shows a mean AUC of 0.72 by randomly splitting the set in 70% training and 30% test and repeating this 50 times. In Table 3, the performance of the BN and the SVM model are compared when features are missing.

TABLE 3

| | Toronto | Ghent | Leuven | Ghent + Leuven |
|---|---|---|---|---|
| SVM with Mean Imputation | 0.69 | 0.71 | 0.68 | 0.69 |
| SVM with BN Imputation | 0.70 | 0.75 | 0.67 | 0.72 |
| BN | 0.70 | 0.77 | 0.72 | 0.75 |

Missing values are imputed as the mean in the first row. The missing values may be the values imputed by the BN model and used in the SVM application in the second row. The BN model infers the missing values from related evidence or values for linked variables. The third row is the BN model. AUC is validated with the three external datasets using all patients.

An SVM model with mean imputation generally performs worse than using the SVM model after using the Bayesian network for imputation. Superior performance is found with the BN model. In Table 4, the performance is shown if patients with missing data are omitted from the validation sets.

TABLE 4

| | Toronto | Ghent | Leuven | Ghent + Leuven |
|---|---|---|---|---|
| SVM with Mean Imputation | 0.70 | 0.74 | 0.76 | 0.73 |
| SVM with BN Imputation | 0.71 | 0.75 | 0.75 | 0.75 |
| BN | 0.71 | 0.75 | 0.82 | 0.77 |

AUC values are provided for three different approaches to missing data of Table 3. SVM whose missing values are imputed by mean, SVM whose missing values are imputed by the BN model, and the BN model infers the missing values. AUC is validated with the three external datasets using only patients in which a complete dataset was available.

As expected, the benefit of the BN model to reason under uncertainty then becomes negligible, and SVM and BN models have much more similar performance. This result shows that it is beneficial to take feature dependence into account while filling in for missing values.

In other embodiments, a Bayesian Network model may predict dyspnea as a radiation side-effect. Different features, like dose variables that are dependent on tumor related factors, may play a determinant role in determining the degree of the unwanted side-effect. Different aspects and stages of a disease may be represented and integrated in one unified framework for personalized medicine.

Various improvements described herein may be used together or separately. Any form of data mining or searching may be used. Although illustrative embodiments have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A system for knowledge-based interpretable predictive modeling of lung cancer patients, the system comprising:

an input configured to receive patient information representing characteristics of a first patient, wherein the characteristics comprise at least two of tumor load, T-stage, N-stage, number of lymph node stations, and WHO performance;

a processor configured to apply a graphical model as a function of the patient information, the model configured to output a prediction for the first patient; and a display configured to output an image, the image comprising a graphical representation of the graphical model and the prediction, wherein the graphical representation shows at least one relationship between the characteristics leading to the prediction.

2. The system of claim 1 wherein the graphical model comprises a Bayesian network with links from a tumor load node to a T-stage node, a N-stage, and a survival node, from the T-stage node to a number of lymph node stations node, from the N-stage node to the number of lymph node stations node, from a WHO score node to the survival node, and from the number of lymph node stations node to the survival node.

3. The system of claim 2 wherein the graphical representation shows the nodes and the links.

4. The system of claim 1 wherein the graphical model comprises a model for non-small cell lung cancer.

5. The system of claim 1 wherein the graphical model is a machine-learned Bayesian network with a seed for training the graphical model provided from an expert in a medical domain and the seed for training representing relationships between variables.

6. The system of claim 1 wherein the output of the model represents a probability for survival through a period.

7. The system of claim 1 wherein the graphical representation includes nodes associated with respective characteristics, a value for each characteristic included with the respective node, and includes links between some nodes and not between other nodes, the links representing relationships of the graphical model.

8. In a computer readable storage medium having stored therein data representing instructions executable by a programmed processor for knowledge-based interpretable predictive modeling of patients, the instructions comprising:

receiving diagram information representing relationships between variables of lung cancer, wherein the variables comprise at least two of tumor load, T-stage, N-stage, number of lymph node stations, WHO performance, and survival, the predictive model trained to predict the survival;

seeding a predictive model with the diagram information;

training the predictive model, as seeded with the diagram information, with training data, the data comprising values for the variables of lung cancer; and displaying a graphical representation of the predictive model after the training, the graphical representation showing at least one of the relationships.

9. The computer readable storage medium of claim 8 further comprising instructions for:

applying the predictive model after the training to patient information for a patient; and displaying a prediction output by the predictive model as a result of the applying and displaying the graphical representation.

10. The computer readable storage medium of claim 8 wherein the predictive model comprises a Bayesian network, and wherein the diagram information includes links from a tumor load node to a T-stage node, a N-stage, and a survival node, from the T-stage node to a number of lymph node stations node, from the N-stage node to the number of lymph node stations node, from a WHO score node to the survival node, and from the number of lymph node stations node to the survival node.

11. The computer readable storage medium of claim 10 wherein the graphical representation shows the nodes and the relationships as links between the nodes.

12. The computer readable storage medium of claim 8 wherein the diagram information is received from an expert in a medical domain.

13. The computer readable storage medium of claim 8 wherein the graphical representation includes nodes associated with respective variables and includes links between some nodes and not between other nodes.

14. A method for knowledge-based interpretable predictive modeling of patients, the method comprising:

training, with machine training using training data for a plurality of previous lung cancer patients, a graphic model to predict survivability of lung cancer based on relationships between variables from a lung cancer expert, the training data including previous patient values for the variables, the variables including the survivability;

applying, with a processor, current patient values of the variables for a current lung cancer patient to the graphic model, the graphic model configured to predict even with one of the variables not having a current patient value as a function of the relationships;

displaying a representation of the graphic model, the representation showing the variables and the relationships remaining after training; and displaying the survivability for the current lung cancer patient predicted by the graphic model, wherein the variables comprise tumor load, T-stage, N-stage, number of lymph node stations, WHO performance, and the survivability.

15. The method of claim 14 wherein the cancer comprises non-small cell lung cancer.

16. The method of claim 14 wherein the graphic model comprises a Bayesian network, and wherein the relationships include links between nodes for the variables.

17. The method of claim 14 wherein the graphic model configured to predict even with one of the variables not having a current patient value comprises using a value associated with a variable in a position of stronger evidence.

18. The method of claim 14 wherein the graphic model configured to predict even with one of the variables not having a current patient value comprises using a substitute value for the one of the variables, the substitute value selected from a distribution learned from the training data.

19. The method of claim 14 further comprising outputting confidence information with the survivability.

* * * * *